United States Patent
Mashima et al.

(10) Patent No.: US 8,871,995 B2
(45) Date of Patent: Oct. 28, 2014

(54) METHOD FOR SCREENING AN AGENT BEING USEFUL FOR THE TREATMENT OF DRY EYE AND/OR CORNEAL AND CONJUNCTIVAL LESION AND PHARMACEUTICAL COMPOSITION OBTAINED BY THE METHOD

(75) Inventors: Yukihiko Mashima, Chiyoda-ku (JP); Akio Siranita, Chiyoda-ku (JP)

(73) Assignee: R-Tech Ueno, Ltd., Tokyo (JP)

( * ) Notice: Subject to any disclaimer, the term of this patent is extended or adjusted under 35 U.S.C. 154(b) by 0 days.

(21) Appl. No.: 13/512,112

(22) PCT Filed: Nov. 26, 2010

(86) PCT No.: PCT/JP2010/071114
§ 371 (c)(1),
(2), (4) Date: May 25, 2012

(87) PCT Pub. No.: WO2011/065475
PCT Pub. Date: Jun. 3, 2011

(65) Prior Publication Data
US 2012/0245090 A1  Sep. 27, 2012

(30) Foreign Application Priority Data
Nov. 27, 2009 (JP) ................................. 2009-270356

(51) Int. Cl.
| | | |
|---|---|---|
| G01N 33/00 | (2006.01) | |
| A01K 67/00 | (2006.01) | |
| A01K 67/027 | (2006.01) | |
| A01K 67/033 | (2006.01) | |
| A61K 49/00 | (2006.01) | |
| A61K 38/00 | (2006.01) | |
| G01N 33/50 | (2006.01) | |
| A61K 38/38 | (2006.01) | |

(52) U.S. Cl.
CPC ...... *G01N 33/5088* (2013.01); *G01N 2800/162* (2013.01); *A61K 38/385* (2013.01); *G01N 2800/16* (2013.01)
USPC ....................... 800/3; 800/9; 800/14; 424/9.2

(58) Field of Classification Search
None
See application file for complete search history.

(56) References Cited

U.S. PATENT DOCUMENTS

| | | | |
|---|---|---|---|
| 4,740,498 A | 4/1988 | Hirao et al. | |
| 5,945,121 A * | 8/1999 | Kato et al. | ................... 424/450 |
| 6,043,213 A * | 3/2000 | Tsubota | ....................... 514/15.2 |
| 6,924,413 B2 * | 8/2005 | Katsuyama | ...................... 800/9 |
| 2003/0041339 A1 | 2/2003 | Katsuyama | |
| 2009/0030001 A1* | 1/2009 | Kimura et al. | ................ 514/245 |
| 2011/0275715 A1* | 11/2011 | Mashima et al. | ............ 514/559 |
| 2012/0087864 A1* | 4/2012 | Mashima et al. | ............ 424/9.2 |
| 2012/0184496 A1* | 7/2012 | Hutchinson et al. | ......... 514/20.5 |

FOREIGN PATENT DOCUMENTS

| | | |
|---|---|---|
| JP | 61-103836 A | 5/1986 |
| JP | 6-271478 A | 9/1994 |
| JP | 2003-102331 A | 4/2003 |
| WO | 97/39769 A | 10/1997 |

OTHER PUBLICATIONS

Toshida et al., "Effect of Retinol Palmitate Eye Drops on Experimental Keratoconjunctival Epithelial Damage Indiced by n-Heptanol in Rabbit," Curr. Eye Res. 33:13-18 (2008).*
International Search Report and Written Opinion of the International Searching Authority dated Jan. 11, 2011 in corresponding PCTJP2010071114.
Burgalassi, S., "Development of a simple dry eye model in the albino rabbit and evaluation of some tear substitutes", Ophthalmic Research, 1999, vol. 31, pp. 229-235.
International Dry Eye Workshop (DEWS), The Ocular Surface, Apr. 2007, vol. 5, No. 2, pp. 65-204.
Extended European Search Report for Application No. 10833321.2-1405 / 2506008 PCT/JP2010071114 dated Apr. 5, 2013.
Toshida Hiroshi et al: Effect of retinol palmitate eye drops on experimental keratoconjunctival epithelial damage induced by n-heptanol in rabbit; Current Eye Research; vol. 33, No. 1, Jan. 2008, pp. 13-18.

* cited by examiner

*Primary Examiner* — James H Alstrum Acevedo
*Assistant Examiner* — Thea D'Ambrosio
(74) *Attorney, Agent, or Firm* — Sughrue Mion, PLLC

(57) ABSTRACT

The present invention provides a method for screening an agent being useful for the treatment of dry eye and/or corneal and conjunctival lesion of dry eye severity level 3 or more according to the report of the International Dry Eye Workshop (DEWS Report) (2007) and a pharmaceutical composition comprising the agent. The present invention further provides a method for the treatment of dry eye and/or corneal and conjunctival lesion of dry eye severity level 3 or more according to DEWS Report (2007) using the agent.

8 Claims, No Drawings

METHOD FOR SCREENING AN AGENT BEING USEFUL FOR THE TREATMENT OF DRY EYE AND/OR CORNEAL AND CONJUNCTIVAL LESION AND PHARMACEUTICAL COMPOSITION OBTAINED BY THE METHOD

CROSS REFERENCE TO RELATED APPLICATIONS

This application is a National Stage of International Application No. PCT/JP2010/071114 filed Nov. 26, 2010 (which claims the priority from Japanese Patent Application No. 2009-270356), the contents of which are incorporated herein by reference in their entirety.

TECHNICAL FIELD

The present invention provides a method for screening an agent being useful for the treatment of dry eye and/or corneal and conjunctival lesion of dry eye severity level 3 or more according to the report of the International Dry Eye WorkShop (DEWS Report) (2007) and a pharmaceutical composition comprising the agent. The present invention further provides a method for the treatment of dry eye and/or corneal and conjunctival lesion dry eye severity level 3 or more according to DEWS Report (2007) using the agent.

BACKGROUND ART

DEWS Report (2007) is a review of current knowledge on dry eye by 70 international experts of dry eye and subcommittees of DEWS provides details of dry eye including definition and classification, epidemiology, diagnosis and monitoring, and management and therapy. The report is published in "The Ocular Surface (APRIL 2007, VOL 5, NO. 2 pp. 65-204)" (non-patent literature herein incorporated by reference) and can be viewed at a website (www.tearfilm.org).

According to DEWS Report (2007), dry eye is defined as follows (see "The Definition and Classification of Dry Eye Disease" (p 75-92)): "Dry eye is a multifactorial disease of the tears and ocular surface that results in symptoms of discomfort, visual disturbance, and tear film instability with potential damage to the ocular surface. It is accompanied by increased osmolarity of the tear film and inflammation of the ocular surface."

Since dry eye is a multifactorial disease as defined above, treatments of dry eye vary depending on its conditions and symptoms. DEWS Report (2007) classifies dry eye severity level into 4 levels (see "Management and Therapy of Dry Eye Disease" (p 163-178) and Table 2 (p 173)) and provides treatment recommendations for each severity level (see "Management and Therapy of Dry Eye Disease" and Table 4) (p 174)).

According to DEWS Report (2007), there are several agents recommended for dry eye severity levels 1 and 2. However, for dry eye severity level 3 or more, particularly for lesion of ocular surface such as cornea and conjunctiva, there is no recommendable agent other than serum. Further, serum should be derived from blood of a patient to be treated (that is, autologous serum) and should be diluted appropriately when administered to eyes.

At present, substantially, there is no effective agent for dry eye of dry eye severity level 3 or more according to DEWS Report (2007). Therefore, it has been required to establish an animal model representing dry eye according to the classification of DEWS Report (2007), in particular dry eye of dry eye severity level 3 or more according to the report, specifically lesion of ocular surface such as cornea and conjunctiva. Also, by using the animal model for drug screening, it has been required to provide a pharmaceutical composition being useful for dry eye of dry eye severity level 3 or more according to DEWS Report (2007), specifically lesion of ocular surface such as cornea and conjunctiva.

PRIOR ART REFERENCES

[Non-patent literature] The Ocular Surface (APRIL 2007, VOL 5, NO. 2 pp. 65-204)

SUMMARY OF INVENTION

Problem to be Solved by the Invention

An object of the present invention is to provide a method for screening an agent being useful for the treatment of dry eye and/or corneal and conjunctival lesion of dry eye severity level 3 or more according to DEWS Report (2007). Further, an object of the present invention is to provide a pharmaceutical composition for the treatment of dry eye and/or corneal and conjunctival lesion as defined above.

Means of Solving the Problem

The instant application provides following inventions:
(1) A method for screening an agent being useful for the treatment of dry eye and/or corneal and conjunctival lesion of dry eye severity level 3 or more according to the report of the International Dry Eye WorkShop (DEWS Report) (2007), which comprises
preparing a model rabbit of corneal and conjunctival lesion having corneal and conjunctival epithelial abrasion by instilling n-heptanol solution to an eye of a rabbit; and
administering a test agent to the eye of the model rabbit and determining an effect of restoring corneal tissue of the test agent.
(2) A pharmaceutical composition for the treatment of dry eye and/or corneal and conjunctival lesion of dry eye severity level 3 or more according to DEWS Report (2007), which comprises an agent obtained by the method of (1).
(3) The pharmaceutical composition of (2), wherein the agent is human albumin.
(4) A pharmaceutical composition for the treatment of dry eye and/or corneal and conjunctival lesion of dry eye severity level 3 or more according to DEWS Report (2007), which comprises human albumin as an active agent.
(5) The pharmaceutical composition of (4), wherein human albumin is human serum albumin.
(6) A method for the treatment of dry eye and/or corneal and conjunctival lesion, which comprises administering an effective amount of an agent obtained by the method of (1) to a patient having dry eye and/or corneal and conjunctival lesion of dry eye severity level 3 or more according to DEWS Report (2007).
(7) A method for the treatment of dry eye and/or corneal and conjunctival lesion, which comprises administering an effective amount of human albumin to a patient having dry eye and/or corneal and conjunctival lesion of dry eye severity level 3 or more according to DEWS Report (2007).
(8) Use of an agent obtained by the method of (1) for the manufacture of a pharmaceutical composition for the treatment of dry eye and/or corneal and conjunctival lesion of dry eye severity level 3 or more according to DEWS Report (2007).

(9) Use of human albumin for the manufacture of pharmaceutical composition for the treatment of dry eye and/or corneal and conjunctival lesion of dry eye severity level 3 or more according to DEWS Report (2007).

Effect of the Invention

According to the instant application, it has become possible to provide a method for screening an agent being useful for the treatment of dry eye and/or corneal and conjunctival lesion of dry eye severity level 3 or more according to DEWS Report (2007). The agent determined as having an effect of restoring corneal tissue according to the screening method of the present invention is useful for the treatment of dry eye and/or corneal and conjunctival lesion of dry eye severity level 3 or more according to DEWS Report (2007. Further, according to the instant application, it has become possible to provide a method for the treatment of dry eye and/or corneal and conjunctival lesion of dry eye severity level 3 or more according to DEWS Report (2007) by using the agent.

DESCRIPTION OF EMBODIMENTS

According to DEWS Report (2007), dry eye severity level is classified as follows (see "Management and Therapy of Dry Eye Disease" (p 163-178) and Table 2 (p 173)).

n-heptanol solution to one of the eyes of the rabbit such that the n-heptanol solution spreads over cornea and bulbar conjunctiva, and forcing the rabbit to blink.

Species of rabbit used in the present invention may be, but not limited to, New Zealand white, Japanese White, and Dutch, and New Zealand white is preferably used. The anesthetic agent administered by intramuscular injection may include ketamine, xylazine, and medetomidine, and preferably, ketamine and xylazine are used in combination. The topical anesthetic agent for ocular administration may include oxybuprocaine, lidocaine, and bupivacaine, and oxybuprocaine is preferably used.

N-heptanol solution instilled into an eye is a solution consisting of n-heptanol only, or a mixture of n-heptanol and ethanol. The mixture of n-heptanol and ethanol is preferred because it has improved hydrophilicity and can easily spread over ocular surface and efficiently induce lesion. Ratio of n-heptanol and ethanol is about 9:1 to about 7:3, preferably about 8:2. The applying volume of n-heptanol solution is about 0.01 to about 0.1 ml, preferably about 0.03 to about 0.05 ml in total and it is preferably instilled in several times (2-4 times) such that the n-heptanol solution efficiently spreads over cornea and bulbar conjunctiva.

After instillation of n-heptanol solution to an eye, the rabbit is forced to blink (1-5 times, preferably 2-4 times), and forced

TABLE 1

Dry eye severity grading scheme

| | Dry Eye Severity Level | | | |
|---|---|---|---|---|
| | 1 | 2 | 3 | 4* |
| Discomfort, severity & frequency | Mild and/or episodic occurs under environ stress | Moderate episodic or chronic, stress or no stress | Severe frequent or constant without stress | Severe and/or disabling and constant |
| Visual symptoms | None or episodic mild fatigue | Annoying and/or activity limiting episodic | Annoying, chronic and/or constant limiting activity | Constant and/or possibly disabling |
| Conjunctival injection | None to mild | None to mild | +/− | +/++ |
| Conjunctival staining | None to mild | Variable | Moderate to marked | Marked |
| Corneal staining (severity/location) | None to mild | Variable | Marked central | Severe punctate erosions |
| Corneal/tear signs | None to mild | Mild debris, ↓ moniscus | Filamentary keratitis, mucus clumping, ↑ tear debris | Filamentary keratitis, mucus clumping, ↑ tear debris, ulceration |
| Lid/meibomian glands | MGD variably present | MGD variably present | Frequent | Trichiasis, keratinization, symblepharon |
| TFBUT (sec) | Variable | ≤10 | ≤5 | Immediate |
| Schirmer score (mm/5 min) | Variable | ≤10 | ≤5 | ≤2 |

*Must have signs AND symptoms.
TBUT: fluorescein tear break-up time.
MGD: meibomian gland disease The "dry eye and/or corneal and conjunctival lesion of dry eye severity level 3 or more according to DEWS Report (2007)" as used in herein refers to dry eye corresponding to dry eye severity level 3 or more according to the above classification, and/or corneal and conjunctival lesion showing any of signs and symptoms of such dry eye.

The term "about" as used herein, when used with any numerical number, refers to +/−30% and +/−20%, and preferably +/−10%.

The model rabbit of corneal and conjunctival lesion used in the screening method of the present invention is prepared by instilling n-heptanol solution to an eye of a rabbit. Generally, the model rabbit may be prepared by anesthetizing a rabbit by intramuscular injection of an anesthetic agent and then by ocular administration of a topical anesthetic agent, instilling to close the eye for several minutes (about 0.5 to about 5 min, preferably about 1 to about 3 min). As a result, corneal and conjunctival epithelial abrasion is occurred. According to the present invention, a stable model of corneal and conjunctival lesion can be prepared.

By determining an effect of restoring corneal tissue of a test agent by using the model rabbit of corneal and conjunctival lesion of the present invention, it is possible to screen an agent being useful for the treatment of dry eye and/or corneal and conjunctival lesion of dry eye severity level 3 or more according to DEWS Report (2007).

In the screening method of the present invention, frequency of ocular administration of a test agent is generally, but not limited to, 1-6 times per day. To determine potency of a test agent regarding the effect of restoring corneal tissue, frequency of ocular administration per day is preferred to be lower and preferably twice per day in general. Duration of ocular administration of a test agent may vary depending on the factors such as timing of the test and species of the rabbit. Generally, the effect of a test agent can be determined in 10 days from the start of its ocular administration.

Generally, the effect of restoring corneal tissue of a test agent may be determined as follows. Conditions of cornea and conjunctiva are observed by staining an eye with a dye before and after instillation of n-heptanol solution; before first-time administration of the test agent on each day; after second-time administration of the test agent on each of days 4, 5, and 6; and one day after the final administration of the test agent. The dye for staining may include fluorescein, rose bengal, and lissamine green and fluorescein is preferably used. Degree of corneal lesion is scored by observing and photographing conditions of corneal staining. A high staining score represents a high degree of corneal lesion and a low staining score represents a low degree of corneal lesion.

For scoring, any conventional method may be used. For example, cornea is divided into 5 areas (central, upper, temporal, nasal and lower areas) and staining intensity of each area is scored out of 3 and the total score (out of 15) is used for determination. Staining intensity is scored 0 for no staining; 1 for partial staining; 2 for staining of about two-third of the area; and 3 for overall staining.

In the present invention, the effect of restoring corneal tissue of a test agent is determined to be significant when significant difference between the staining score showing degree of corneal lesion of the eye administered with the test agent and that of the eye administered with saline is determined at each observation of cornea and conjunctiva and the significance level is less than 5%. Significant difference may be determined by any method appropriately, and for example, by Paired Student's t-test.

For agents each recommended for dry eye severity level 1, 2 or 3 in DEWS Report (2007), the effect of restoring corneal tissue was confirmed by using the model rabbit of corneal and conjunctival lesion of the present invention. Agents recommended in DEWS Report (2007) for dry eye severity levels 1 and 2, such as a formulation containing viscous component (Hyalein® mini ophthalmic solution 0.3%: Santen Pharmaceutical (Japan): approved in Japan) or a formulation containing electrolyte (Cationorm®: Novagali Pharma (France): approved in EU) for dry eye severity level 1, and a formulation containing an anti-inflammatory agent (Restasis®: Allergen (US): approved in US) for dry eye severity level 2, did not show a significant effect of restoring corneal tissue. On the other hand, serum, which is recommended for dry eye severity level 3 (human serum pools: Kohjin Bio (Japan)) showed a significant effect of restoring corneal tissue. Accordingly, the method of determining the effect of restoring corneal tissue by using the model rabbit of corneal and conjunctival lesion of the present invention is understood to be useful for screening an agent being useful for the treatment of dry eye and/or corneal and conjunctival lesion of dry eye severity level 3 or more according to DEWS Report (2007).

Further, according to the screening method of the present invention, it has been revealed that human serum albumin has a significant effect of restoring corneal tissue in the model rabbit of corneal and conjunctival lesion of the present invention, similar to the agent recommended in DEWS Report (2007) for dry eye severity level 3 (serum). Therefore, humen albumin is understood to be useful for the treatment of dry eye and/or corneal and conjunctival lesion of dry eye severity level 3 or more according to DEWS Report (2007).

In the present invention, human albumin is preferably human serum albumin. Any human serum albumin may be used in the present invention, on condition that it has purity for general medical purpose. Specifically, it is preferred to contain albumin 80% or more when analyzed by electrophoresis. In addition, it is preferred to be heat-treated for inactivation of virus or others. Particularly, human serum albumin commercially available as a medicament is preferred. Recombinant human serum albumins produced by microorganisms are also preferably used for the present invention. Methods for preparing recombinant human serum albumins using gene-recombination technology are well known in the art. For example, a vector containing a gene encoding human serum albumin is prepared and introduced into host cells such that the cells are transformed. Then, transformed cells producing human serum albumin are selected and cultured, and from the cells or the culture media thereof, human serum albumin is isolated and purified. The host cell may include microorganisms commonly used in the art for protein production, such as yeasts and *E. Coli*. Examples of yeasts may include those belonging to the genus *Kluyveromyces, Saccharomyces* and *Pichia*, and in particular, *Kluyveromyces laactis, Saccharomyces cerevisiae,* and *Pichia pastoris* are preferably used. It is still preferable to use *Kluyveromyces laactis* CBS2360 strain, *Saccharomyces cerevisiae* AH22 strain (a, his 4, leu 2, can 1) and *Pichia pastoris* GTS115 strain (his 4) as the host yeast.

As used herein, the term "treatment" or "treating" refers to any means of control of the conditions, including prevention, cure and relief of the conditions and arrestation or relief of development of the condition.

The pharmaceutical composition of the present invention may be in any dosage form for topical administration to eyes. It is particularly preferred to be ophthalmic solutions or eye drops.

In case of the composition of the present invention is formulated as an ophthalmic solution comprising human albumin as an active agent, the composition may contain human albumin in an amount of about 1 to 1000 mg/ml (0.1-100 w/v %), more preferably about 10 to 1000 mg/ml (1-100 w/v %), and especially, about 10 to 250 mg/ml (1-25 w/v %). The composition may further contain a pharmaceutically acceptable diluent.

As used herein, the "pharmaceutically acceptable diluent" may be any diluent which is used for ophthalmic composition known to persons skilled in the art, for example, water, physiological saline, artificial tear solution, and the like. The pharmaceutical composition of the present invention may further comprise various components that are generally used in ophthalmic compositions, such as stabilizers, sterilizers, buffering agents, isotonic agents, chelating agents, pH adjusters, surfactants, and the like. When the composition is formulated as an ophthalmic solution or eye drops, the pH of the composition is preferably adjusted from 5 to 8.

The pharmaceutical composition of the present invention may be administered in an amount of about 1 to about 100 μl/eye, preferably about 10 to about 50 μl/eye, and more preferably about 30 to 50 μl/eye for one administration.

In a different aspect, the present invention provides use of human albumin for the manufacture of a pharmaceutical composition for the treatment of dry eye and/or corneal and conjunctival lesion of dry eye severity level 3 or more according to DEWS Report (2007).

In a further different aspect, the present invention provides a method for the treatment of dry eye and/or corneal and conjunctival lesion of dry eye severity level 3 or more according to DEWS Report (2007), which comprises administering to a subject in need thereof an effective amount of human albumin.

In these methods of the present invention, the "effective amount" of human albumin is an amount required for the desirable treatment, and may be selected an optimum according to the patient's symptoms, age, sex, body weight, diet, other drugs used in combination and various factors which are recognized by persons skilled in the medical field. This effective amount may also vary depending on the kind or activity of human albumin, in addition to the above factors. In these methods of the present invention, the pharmaceutical composition may be administered in an amount of about 1 to about 100 µl/eye, preferably about 10 to about 50 µl/eye and more preferably about 30 to 50 µl/eye, about 1 to about 20 times per day and more preferably, 1 to 10 times per day, but it is not intended to limit the scope of the invention.

The pharmaceutical composition used in the present invention may be co-administered with other pharmaceutically active compound unless it does not interfere with the effect of the present invention. The term "co-administer" may include to administer the other pharmaceutically active compound before, simultaneously with and after administering the pharmaceutical composition of the present invention. When the other pharmaceutically active compound is administered simultaneously with the pharmaceutical composition of the present invention, the composition of the present invention and the other compound may be formulated together in single dosage form or respectively in separate dosage forms. For example, artificial tear solution, polysaccharide sulfate such as hyaluronic acid and chondroitin sulfate, cyclosporine, glutathione, flavin-adenine nucleotide sodium, corticosteroid, tetracycline, vitamin A (retinol) and its derivatives such as vitamin A esters including retinol palmitate and retinol acetate, and cell growth factor such as hepatocyte growth factor (HGF), epidermal growth factor (EGF), fibroblast growth factor (FGF), insulin-like growth factor (IGF), nerve growth factor (NGF), platelet-derived growth factor (PDGF), transforming growth factor (TGF-$\alpha$ and TGF-3) and keratinocyte growth factor (KGF) may be co-administered with the pharmaceutical composition of the present invention.

The present invention will be further explained in view of test examples shown below. The test examples should not be used for limiting the scope of the instant application in any means.

EXAMPLES

Test Example 1

Preparation of Corneal and Conjunctival Lesion Model

Rabbits (std:NZW) was anesthetized by intramuscular injection of ketamine (10 mg/kg) and xylazine (4 mg/kg) and then by ocular administration of 0.4% oxybuprocaine (2 drops per eye). The rabbits were held in a recumbent position and instilled 0.04 ml (0.01 ml×4 times) of n-heptanol solution (n-heptanol: ethanol=8:2), prepared just before use, into one of eyes such that the n-heptanol solution spreads over cornea and bulbar conjunctiva. Then, the rabbits were forced to blink 3 times and to close the eyes for 2 min after the third blinking. The both eyes were given this process. Thus, models of corneal and conjunctival lesion were prepared.

(Administration of Test Agents)

Starting from the day of preparation of corneal and conjunctival lesion, serum or 0.3% sodium hyaluronate formulation was administered repeatedly 2 times per day for 10 days. Saline was administered in a same manner to the other eyes than those administered with the test agent. They were all administered in a volume of 50 µl/eye/time.

For use as serum, human serum pools (Kohjin Bio (Japan)) was sterilized by filtration (MILLEX GV, PVDF, 0.22 µm, MILLIPORE) and diluted 5 times with saline according to the method known to prepare serum ophthalmic solution used in autologous serum therapy for dry eye.

The 0.3% sodium hyaluronate formulation was Hyalein® mini ophthalmic solution 0.3% (Santen Pharmaceutical (Japan)).

(Test Groups)

TABLE 2

| Group | Test agent | number of eyes (number of cases) |
|---|---|---|
| 1 | Serum | 6 eyes (6 animals) |
| 2 | 0.3% sodium hyaluronate | 6 eyes (6 animals) |

The rabbits were allocated to each group by stratified randomization on body weight.

(Determination of Corneal Lesion)

Conditions of corned and conjunctiva were observed before treatment of n-heptanol solution (one day before the first administration of the test agent); just after treatment of n-heptanol solution; before first-time administration of the test agent on each day; after second-time administration of the test agent on each of days 4, 5, and 6; and one day after the final administration of the test agent.

Two µl of 1% fluorescein was instilled into the eyes. After 2 mins, staining of cornea and conjunctiva was photographed and observed by a digital microscope (VHX-900, KEYENCE CORPORATION (Japan)) with a cobalt blue filter (FUJI FILTER BPB45) in the light emitting section and a yellow filter (FUJI FILTER SC52) in front of the tense, and then degree of corneal lesion was scored. For scoring, each cornea was divided into 5 areas (central, upper, temporal, nasal and lower areas). Staining intensity with fluorescein of each area was scored out of 3 and the total score (out of 15) was used for determination. Staining intensity was scored 0 for no staining; 1 for partial staining; 2 for staining of about two-third of the area; and 3 for overall staining.

The 1% fluorescein was prepared by dissolving fluorescein sodium salt with saline.

(Result)

Scores of fluorescein staining of cornea after the treatment of n-heptanol solution were shown in Table 3. In ail animals, scores of fluorescein staining of cornea before the treatment of n-heptanol solution were 0.

As shown in Table 3, in the eyes administered with serum, a significant effect of restoring corneal epithelium ($p<0.05$) was observed on day 4 of the treatment of lesion.

On the other hand, no effect of restoring corneal epithelium was observed with the administration of 0.3% sodium hyaluronate.

TABLE 3

Fluorescein scores in cornea of rabbits with n-heptanol-induced keratoconjunctival injury after repeat administration of serum or 0.3% hyaluronate to one eye and saline to the other eye 2 times per day for 10 days.

| Test group | | Day | 0 | 1 | 2 | 3 | 3.5 | 4 | 4.5 | 5 | 5.5 | 6 | 7 | 8 | 9 | 10 |
|---|---|---|---|---|---|---|---|---|---|---|---|---|---|---|---|---|
| 1 | Serum | mean | 15.00 | 15.00 | 15.00 | 15.00 | 14.17 | 13.33 * | 12.17 | 10.00 | 8.67 | 6.33 | 5.17 | 3.50 | 2.17 | 1.50 |
| | | SE | 0.00 | 0.00 | 0.00 | 0.00 | 0.48 | 0.76 | 1.05 | 1.00 | 0.85 | 0.88 | 1.01 | 1.18 | 0.87 | 0.43 |
| | Saline | mean | 15.00 | 15.00 | 15.00 | 15.00 | 14.83 | 14.67 | 13.00 | 11.00 | 9.17 | 7.50 | 5.83 | 4.50 | 2.50 | 1.83 |
| | | SE | 0.00 | 0.00 | 0.00 | 0.00 | 0.17 | 0.33 | 0.68 | 1.13 | 1.05 | 0.89 | 0.87 | 0.56 | 0.62 | 0.40 |
| 2 | 0.3% sodium hyaluronate | mean | 15.00 | 15.00 | 15.00 | 15.00 | 14.67 | 14.17 | 12.50 | 10.17 | 7.50 | 6.83 | 4.50 | 2.50 | 2.00 | 1.33 |
| | | SE | 0.00 | 0.00 | 0.00 | 0.00 | 0.21 | 0.48 | 0.80 | 1.25 | 1.23 | 1.08 | 0.89 | 0.56 | 0.86 | 0.85 |
| | Saline | mean | 15.00 | 15.00 | 15.00 | 15.00 | 15.00 | 13.83 | 12.83 | 11.17 | 7.67 | 6.33 | 4.67 | 2.83 | 1.33 | 1.17 |
| | | SE | 0.00 | 0.00 | 0.00 | 0.00 | 0.00 | 0.54 | 0.60 | 0.70 | 0.92 | 0.71 | 0.85 | 0.17 | 0.42 | 0.40 |

Day 0: The day of treatment of n-heptanol (the day of starting administration of test agents)
Each cornea was divided into 5 areas, scored out of 3 and evaluated with the total score (out of 15).
The smaller the number was, the higher the restoring effect was.
*, ** Paired Student's t-test, p < 0.05 (*), 0.01 (**).

Test Example 2

Preparation of corneal and conjunctival lesion model, administration of test agents, and determination of corneal lesion were performed as described in Test Example 1.

The test agent was 0.05% cyclosporine formulation or cationic emulsion. As 0.05% cyclosporine formulation, Restasis® (Allergan, Inc (US)) was used. As cationic emulsion, Cationorm® (Novagali Pharma SA (France)) was used.

(Test Groups)

TABLE 4

| Group | Test agent | number of eyes (number of cases) |
|---|---|---|
| 1 | 0.05% cyclosporine | 6 eyes (6 animals) |
| 2 | cationic emulsion | 6 eyes (6 animals) |

The rabbits were allocated to each group by stratified randomization on body weight.

(Result)

Scores of fluorescein staining of cornea after the treatment of n-heptanol solution were shown in Table 5. In all animals, scores of fluorescein staining of cornea before the treatment of n-heptanol solution were 0.

As shown in Table 5, administration of any of 0.05% cyclosporine and cationic emulsion did not show an effect of restoring corneal epithelium.

According to the results of Test Examples 1 and 2, it was confirmed that the agent recommended in DEWS Report (2007) for dry eye severity level 3 (serum), but not the agents recommended for dry eye severity levels 1 and 2, shows a significant effect of restoring corneal tissue in the determination system using the model rabbit of the present invention. Accordingly, the model rabbit of corneal and conjunctival lesion of the present invention is understood to be useful as a model animal representing dry eye according to the classification of DEWS Report (2007), particularly dry eye of dry eye severity level 3 or more according to the report, specifically lesion of ocular surface such as cornea and conjunctiva.

TABLE 5

Fluorescein scores in cornea of rabbits with n-heptanol-induced keratoconjunctival injury after repeat administration of 0.05% cyclosporine formulation or cationic emultion to one eye and saline to the other eye 2 times per day for 10 days.

| Test group | | Day | 0 | 1 | 2 | 3 | 3.5 | 4 | 4.5 | 5 | 5.5 | 6 | 7 | 8 | 9 | 10 |
|---|---|---|---|---|---|---|---|---|---|---|---|---|---|---|---|---|
| 1 | 0.05% cyclosporine | mean | 15.00 | 15.00 | 15.00 | 15.00 | 14.50 | 13.17 | 11.67 | 10.17 | 9.17 | 7.17 | 5.67 | 5.00 | 3.33 | 3.67 |
| | | SE | 0.00 | 0.00 | 0.00 | 0.00 | 0.22 | 0.70 | 1.05 | 0.98 | 0.83 | 0.87 | 0.76 | 0.86 | 1.02 | 0.92 |
| | Saline | mean | 15.00 | 14.83 | 14.50 | 14.33 | 13.50 | 12.00 | 9.83 | 8.50 | 7.00 | 3.83 | 3.00 | 1.83 | 1.67 | |
| | | SE | 0.00 | 0.00 | 0.17 | 0.50 | 0.49 | 0.96 | 1.07 | 1.35 | 1.43 | 1.55 | 0.98 | 1.34 | 1.11 | 0.62 |
| 2 | Cationic emulsion | mean | 15.00 | 15.00 | 15.00 | 15.00 | 14.50 | 14.17 | 12.67 | 10.17 | 9.33 | 7.50 | 5.33 | 4.33 | 2.33 | 2.67 |
| | | SE | 0.00 | 0.00 | 0.00 | 0.00 | 0.34 | 0.40 | 0.96 | 1.35 | 1.11 | 0.99 | 1.23 | 1.14 | 1.11 | 1.31 |
| | Saline | mean | 15.00 | 15.00 | 15.00 | 15.00 | 15.00 | 14.50 | 13.50 | 11.00 | 9.67 | 8.67 | 5.50 | 4.17 | 2.50 | 2.17 |
| | | SE | 0.00 | 0.00 | 0.00 | 0.00 | 0.00 | 0.34 | 0.56 | 1.07 | 1.11 | 1.54 | 1.41 | 1.45 | 1.36 | 1.28 |

Day 0: The day of treatment of n-heptanol (the day of starting administration of test agents)
Each cornea was divided into 5 areas, scored out of 3 and evaluated with the total score (out of 15).
The smaller the number was, the higher the restoring effect was.

Test Example 3

Preparation of corneal and conjunctival lesion model, administration of test agents, and determination of corneal lesion were performed as described in Test Example 1.

The test agent was 10% nHSA.

For use as 10% nHSA, Kenketsu albumin-Wf (25% human serum albumin formulation, Mitsubishi Tanabe Pharma) was diluted with sodium chloride solution such that osmotic pressure was almost equal to saline.

(Test Groups)

TABLE 6

| Group | Test agent | number of eyes (number of cases) |
|---|---|---|
| 1 | 10% nHSA | 6 eyes (6 animals) |

(Result)

Scores of fluorescein staining of cornea after the treatment of n-heptanol solution were shown in Table 7. In all cases, scores of fluorescein staining of cornea before the treatment of n-heptanol solution were 0.

As shown in Table 7, scores of fluorescein staining of cornea were significantly lowered with the administration of 10% nHSA compared to saline on days 4, 4.5, 5, 5.5, 6 and 10 of the treatment of lesion, indicating the effect of restoring corneal epithelium of 10% nHSA (Days 4, 5, 5.5, 6, and 10: $p<0.05$; Day 4.5: $p<0.01$).

According to the above result, it is understood that human serum albumin has an effect of restoring corneal tissue equal to or more than that of serum which is recommended in DEWS Report (2007) for dry eye severity level 3 (Test Example 1).

Dry eye severity grading scheme

| | Dry Eye Severity Level | |
|---|---|---|
| | 1 | 2 |
| Discomfort, severity & frequency | Mild and/or episodic occurs under environ stress | Moderate episodic or chronic stress or no stress |
| Visual symptoms | None or episodic mild fatigue | Annoying and/or activity limiting episodic |
| Conjunctival injection | None to mild | None to mild |
| Conjunctival staining | None to mild | Variable |
| Corneal staining (severity/location) | None to mild | Variable |
| Corneal/tear signs | None to mild | Mild debris, ↓ meniscus |
| Lid/meibomian glands | MGD variably present | MGD variably present |
| TFBUT (sec) | Variable | ≤10 |
| Schirmer score (mm/5 min) | Variable | ≤10 |

| | Dry Eye Severity Level | |
|---|---|---|
| | 3[#] | 4[*] |
| Discomfort, severity & frequency | Severe frequent or constant without stress | Severe and/or disabling and constant |
| Visual symptoms | Annoying, chronic and/or constant limiting activity | Constant and/or possibly disabling |
| Conjunctival injection | +/− | +/++ |
| Conjunctival staining | Moderate to marked | Marked |
| Corneal staining (severity/location) | Marked central | Severe punctate erosions |
| Corneal/tear signs | Filamentary keratitis, mucus clumping, ↑ tear debris | Filamentary keratitis, mucus clumping, ↑ tear debris, ulceration |
| Lid/meibomian glands | Frequent | Trichiasis, keratinization, symolepharon |
| TFBUT (sec) | ≤5 | Immediate |
| Schirmer score (mm/5 min) | ≤5 | ≤2 |

[#]Must show at least one of signs and symptoms.
[*]Must have signs AND symptoms.
TFBUT: fluorescein tear break-up time.
MGD: meibomian gland disease.

TABLE 7

Fluorescein scores in cornea of rabbits with n-heptanol-induced keratoconjunctival injury after repeat administration of 10% nHSA to one eye and saline to the other eye 2 times per day for 10 days.

| Test group | | Day | 0 | 1 | 2 | 3 | 3.5 | 4 | 4.5 | 5 | 5.5 | 6 | 7 | 8 | 9 | 10 |
|---|---|---|---|---|---|---|---|---|---|---|---|---|---|---|---|---|
| | | | | | | | | Scores of fluorescein staining (mean and standard error of 6 cases) | | | | | | | | |
| 1 | 10% nHSA | mean | 15.00 | 15.00 | 15.00 | 14.83 | 13.83 | 12.83 * | 11.00 ** | 7.17 * | 6.17 * | 4.83 * | 3.17 | 1.83 | 1.50 | 1.50 * |
| | | SE | 0.00 | 0.00 | 0.00 | 0.17 | 0.54 | 0.70 | 1.03 | 0.83 | 0.95 | 0.48 | 0.87 | 0.48 | 0.43 | 0.50 |
| | Saline | mean | 15.00 | 15.00 | 15.00 | 15.00 | 14.67 | 14.33 | 13.17 | 10.50 | 8.67 | 6.67 | 4.50 | 2.83 | 2.00 | 2.50 |
| | | SE | 0.00 | 0.00 | 0.00 | 0.00 | 0.33 | 0.49 | 0.95 | 1.20 | 1.36 | 0.80 | 0.85 | 0.79 | 0.51 | 0.43 |

Day 0: The day of treatment of n-heptanol (the day of starting administration of test agents)
Each cornea was divided into 5 areas, scored out of 3 and evaluated with the total score (out of 15).
The smaller the number was, the higher the restoring effect was.

The invention claimed is:

1. A method for screening an agent being useful for the treatment of dry eye and/or corneal and conjunctival lesion of dry eye severity level 3 or more according to the table below:

wherein said method comprises
- preparing a model rabbit of corneal and conjunctival lesion having corneal and conjunctival epithelial abrasion by instilling n-heptanol solution to an eye of a rabbit such that the n-heptanol solution spreads over cornea and bulbar conjunctiva, and forcing the rabbit to blink; and
- administering a test agent to the eye of the model rabbit and determining an effect of restoring corneal tissue of the test agent by (i) staining the eye with a dye to show corneal lesion and (ii) observing a change in amount of staining in the eye over time, wherein an agent that is useful for said treatment reduces the amount of staining in the eye over time,
- wherein the preparing step further comprises forcing the rabbit to close the eye for about 1 to about 3 minutes.

2. The method according to claim 1, wherein the n-heptanol solution is a mixture of n-heptanol and ethanol.

3. The method according to claim 2, wherein the n-heptanol and ethanol are present in a ratio of n-heptanol:ethanol of from about 9:1 to about 7:3.

4. The method according to claim 3, wherein the ratio is about 8:2.

5. The method according to claim 1, wherein the n-heptanol solution is applied in a volume of about 0.01 to about 0.1 ml.

6. The method according to claim 1, wherein the n-heptanol solution is applied in a volume of about 0.03 to about 0.05 ml.

7. The method according to claim 1, wherein the n-heptanol solution is instilled 2-4 times.

8. The method according to claim 1, wherein the rabbit is forced to blink 2-4 times.

* * * * *